United States Patent
Lee

(10) Patent No.: US 11,937,837 B2
(45) Date of Patent: Mar. 26, 2024

(54) FIBRIN RICH / SOFT CLOT MECHANICAL THROMBECTOMY DEVICE

(71) Applicant: Neuravi Limited, Galway (IE)

(72) Inventor: Declan Lee, Galway (IE)

(73) Assignee: NEURAVI LIMITED, Galway (IE)

( * ) Notice: Subject to any disclaimer, the term of this patent is extended or adjusted under 35 U.S.C. 154(b) by 357 days.

(21) Appl. No.: 17/136,346

(22) Filed: Dec. 29, 2020

(65) Prior Publication Data

US 2022/0202428 A1  Jun. 30, 2022

(51) Int. Cl.
*A61B 17/221* (2006.01)
*A61M 25/00* (2006.01)
*A61B 17/00* (2006.01)

(52) U.S. Cl.
CPC .. *A61B 17/221* (2013.01); *A61B 2017/00526* (2013.01); *A61B 2017/2212* (2013.01); *A61M 2025/0079* (2013.01)

(58) Field of Classification Search
CPC ........ A61B 17/221; A61B 2017/00526; A61B 2017/2212; A61B 17/22031; A61B 2017/22034; A61B 2017/22035; A61B 2017/2215; A61B 2017/2217; A61M 2025/0079; A61F 2/013; A61F 2002/015; A61F 2002/016; A61F 2002/018
USPC ....................................................... 606/159
See application file for complete search history.

(56) References Cited

U.S. PATENT DOCUMENTS

| | | |
|---|---|---|
| 4,455,717 A | 6/1984 | Gray |
| 4,611,594 A | 9/1986 | Grayhack et al. |
| 4,612,931 A | 9/1986 | Dormia |
| 4,643,184 A | 2/1987 | Mobin-Uddin |
| 4,727,873 A | 3/1988 | Mobin-Uddin |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | MacGregor et al. |
| 5,092,839 A | 3/1992 | Kipperman |

(Continued)

FOREIGN PATENT DOCUMENTS

| | | |
|---|---|---|
| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)

*Primary Examiner* — Kankindi Rwego
(74) *Attorney, Agent, or Firm* — TROUTMAN PEPPER HAMILTON SANDERS LLP

(57) ABSTRACT

Designs are disclosed for devices capable of removing both firm and soft clots from body vessels that can have dual layers where an inner expandable body of cells runs within an outer expandable cage of cells. The designs can feature a constrained delivery configuration and an expanded deployed configuration. An outer cage can have wide opening struts to allow for clot integration into the device. Both the inner body and outer cage can be configured with shapes to pinch a clot in addition to embedding in it. The devices can also be capable of having a portion of the outer cage fold and invert proximally after engaging with a target clot to internalize it. These factors can increase the device's ability to capture clots of all compositions, allowing for safer and more efficient flow restoration.

9 Claims, 7 Drawing Sheets

(56) References Cited

U.S. PATENT DOCUMENTS

| | | |
|---|---|---|
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,733,325 A | 3/1998 | Robinson et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,824,041 A | 10/1998 | Lenker et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |

(56) References Cited

U.S. PATENT DOCUMENTS

| | | |
|---|---|---|
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,241,308 B2 | 7/2007 | Andreas et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Landau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |

(56) References Cited

U.S. PATENT DOCUMENTS

| | | |
|---|---|---|
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,517,340 B2 | 12/2022 | Casey |
| 2001/0001315 A1 | 5/2001 | Bates et al. |
| 2001/0016755 A1 | 8/2001 | Addis |
| 2001/0037141 A1 | 11/2001 | Yee et al. |
| 2001/0041909 A1 | 11/2001 | Tsugita et al. |
| 2001/0044632 A1* | 11/2001 | Daniel ............ A61B 17/22031 606/200 |
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zando-Azizi et al. |
| 2002/0095171 A1 | 7/2002 | Belef |
| 2002/0123765 A1 | 9/2002 | Sepetka et al. |
| 2002/0128680 A1 | 9/2002 | Pavolvic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |

(56) References Cited

U.S. PATENT DOCUMENTS

| | | |
|---|---|---|
| 2003/0040772 A1 | 2/2003 | Hyodoh et al. |
| 2003/0050663 A1 | 3/2003 | Khachin et al. |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0204749 A1 | 10/2004 | Gunderson |
| 2004/0215318 A1 | 10/2004 | Kwitkin |
| 2004/0220663 A1 | 11/2004 | Rivelli |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0171566 A1 | 8/2005 | Kanamaru |
| 2005/0192627 A1 | 9/2005 | Whisenant et al. |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman |
| 2006/0069424 A1 | 3/2006 | Acosta et al. |
| 2006/0074477 A1 | 4/2006 | Berthiaume et al. |
| 2006/0142838 A1 | 6/2006 | Molaei et al. |
| 2006/0149313 A1 | 7/2006 | Arguello et al. |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0112374 A1* | 5/2007 | Paul, Jr. ............... A61F 2/013 606/200 |
| 2007/0118173 A1 | 5/2007 | Magnuson et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0262590 A1 | 10/2008 | Murray |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |

(56) References Cited

U.S. PATENT DOCUMENTS

| | | |
|---|---|---|
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0270374 A1 | 11/2011 | Orr et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0022572 A1 | 6/2012 | Braun et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158591 A1 | 6/2013 | Koehler |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |

(56) References Cited

U.S. PATENT DOCUMENTS

| | | |
|---|---|---|
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1* | 3/2017 | Vale ................. A61F 2/013 |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm, III |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1* | 7/2017 | Cox ................. A61B 17/221 |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1 | 12/2020 | Casey et al. |
| 2021/0005321 A1 | 1/2021 | Hwang |
| 2021/0007757 A1 | 1/2021 | Casey et al. |
| 2021/0228223 A1 | 7/2021 | Casey et al. |

FOREIGN PATENT DOCUMENTS

| | | |
|---|---|---|
| CN | 102307613 A | 1/2012 |
| CN | 102316809 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |

(56) References Cited

FOREIGN PATENT DOCUMENTS

| | | |
|---|---|---|
| EP | 1153581 A1 | 11/2001 |
| EP | 2301450 A1 | 3/2011 |
| EP | 2438891 A1 | 4/2012 |
| EP | 2628455 A1 | 8/2013 |
| EP | 3156004 A1 | 4/2017 |
| EP | 3593742 A1 | 1/2020 |
| EP | 3669802 A1 | 6/2020 |
| EP | 3858291 A1 | 8/2021 |
| GB | 2427554 A | 1/2007 |
| GB | 2494820 A | 3/2013 |
| JP | 09-19438 A | 1/1997 |
| JP | 2014-511223 A | 5/2014 |
| JP | 2014-525796 A | 10/2014 |
| JP | 2015-505250 A | 2/2015 |
| JP | 2016-513505 A | 5/2016 |
| JP | 2019-526365 A | 9/2019 |
| NO | WO 2013/072777 A2 | 5/2013 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/030751 A1 | 4/2003 |
| WO | WO 03/051448 A2 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A1 | 5/2007 |
| WO | WO 2007/068424 A2 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2008/135823 A1 | 11/2008 |
| WO | WO 2009/031338 A1 | 3/2009 |
| WO | WO 2009/076482 A1 | 6/2009 |
| WO | WO 2009/086482 A1 | 7/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/105099 A2 | 7/2013 |
| WO | WO 2013/109756 A2 | 7/2013 |
| WO | WO 2013/187927 A1 | 12/2013 |
| WO | WO 2014/047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/103547 A1 | 7/2015 |
| WO | WO 2015/134625 A1 | 9/2015 |
| WO | WO 2015/179324 A2 | 11/2015 |
| WO | WO 2015/189354 A1 | 12/2015 |
| WO | WO 2016/010995 A1 | 1/2016 |
| WO | WO 2016/089451 A1 | 6/2016 |
| WO | WO 2017/089424 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

\* cited by examiner

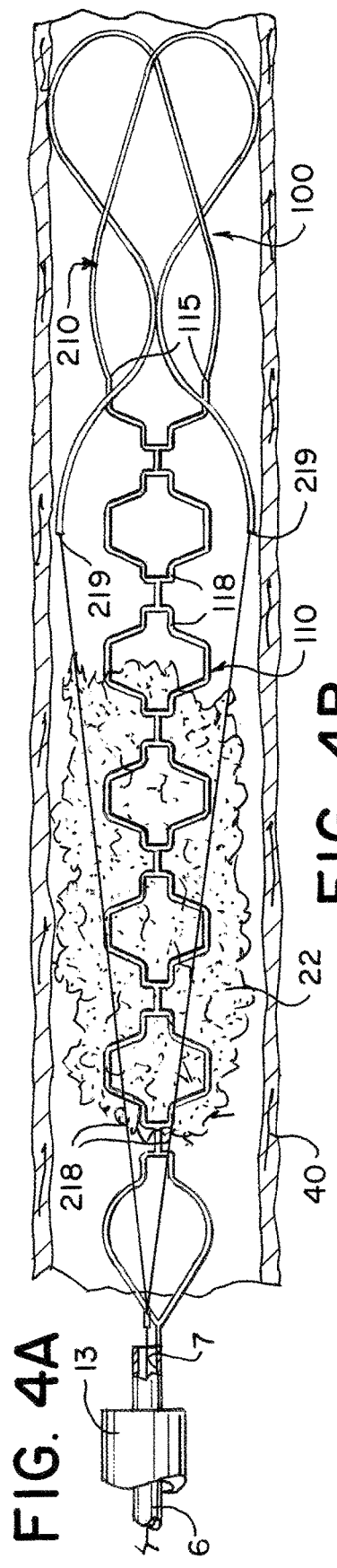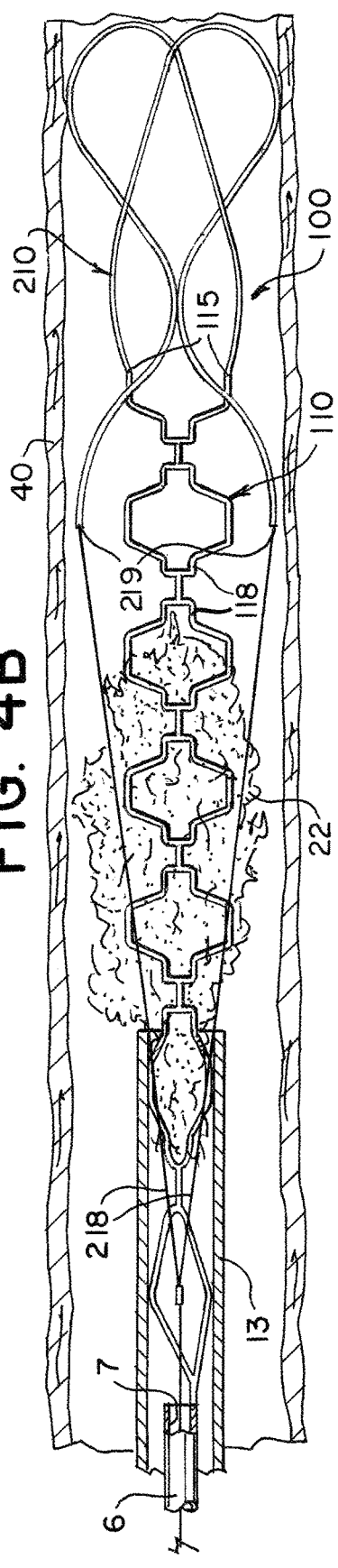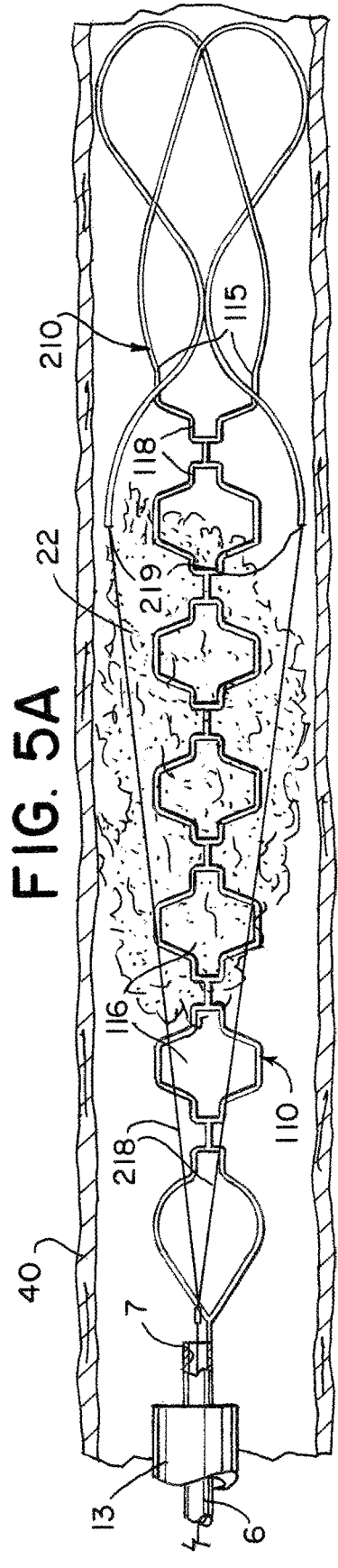

FIBRIN RICH / SOFT CLOT MECHANICAL THROMBECTOMY DEVICE

FIELD OF THE INVENTION

The present disclosure generally relates to devices and methods for removing acute blockages from body vessels during intravascular medical treatments. More specifically, the present disclosure relates to a clot retrieval device for removing a clot from a blood vessel.

BACKGROUND

Mechanical devices and methods can be used for removing acute obstructions from blood vessels. Acute obstructions may include a clot, misplaced devices, migrated devices, large emboli, and the like. Thromboembolism occurs when part or all of a thrombus breaks away from the blood vessel wall. This clot (now called an embolus) is then carried in the direction of blood flow, which can result in many complications. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus, and this mechanism is common in the formation of coronary blockages. The devices and methods herein are particularly suited to removing clots from cerebral arteries in patients suffering acute ischemic stroke (AIS), from pulmonary arteries in patients suffering from pulmonary embolism (PE), from coronary native or graft vessels in patients suffering from myocardial infarction (MI), and from other peripheral arterial and venous vessels in which a clot is causing an occlusion.

There are a number of access challenges that can make it difficult to deliver devices to a target site. In cases where access involves navigating the aortic arch (such as coronary or cerebral blockages) the configuration of the arch in some patients makes it difficult to position a guide catheter. The tortuosity challenge is even more severe in the arteries approaching the brain. It is not unusual at the distal end of the internal carotid artery that the device will have to navigate a vessel segment with several extreme bends in quick succession over only a few centimeters of travel. In the case of pulmonary embolisms, access may be gained through the venous system and then through the right atrium and ventricle of the heart. The right ventricular outflow tract and pulmonary arteries are delicate vessels that can easily be damaged by inflexible or high-profile devices. For these reasons it is desirable that a clot retrieval device be compatible with as low profile and flexible access catheters as possible.

Stent-like clot retriever devices are being increasingly used to remove a clot from cerebral vessels of acute stroke patients. These devices often rely on a pinning mechanism to grab the clot by trapping it between the self-expanding stent-like body and the vessel wall. This approach has a number of disadvantages.

A stent-like clot retriever depends on its outward radial force to retain its grip on the clot during retraction. This compressive force will tend to dehydrate the clot, which in turn can increase its coefficient of friction, making it more difficult to dislodge and remove from the vessel. If the radial force is too low the stent-like clot retriever can lose its grip on the clot, but if the radial force is too high the stent-like clot retriever may damage the vessel wall and require too much force to withdraw. Therefore stent-like clot retrievers that have sufficient radial force to deal with all clot types may cause vessel trauma and serious patient injury, and stent-like clot retrievers that have appropriate radial force to remain atraumatic may not be able to effectively handle all clot types in diverse thrombectomy situations. Pinning the clot between the stent-like clot retriever and the vessel wall also results in high shear forces against the side of the clot as it is removed, potentially releasing fragments of the clot. If these fragments are not retained by the device, they may migrate leading to further blockages in the distal vasculature.

Certain conventional thrombectomy device designs also do not retain their expanded shape very well when placed in tension in vessel bends, due to the manner in which their strut elements are connected to one another which results in the struts being placed in tension during retraction. This tension is due to friction between the device and the blood vessel and is increased if an additional load is applied load such as the resistance provided by a clot. This can result in a loss of grip on the clot as the stent-like clot retriever is withdrawn proximally around a bend in a tortuous vessel, with the potential for the captured clot to escape. In a bend, the struts on the outside of the bend are placed in higher tension than those on the inside. In order to attain the lowest possible energy state, the outside surface of the clot retrieval device moves towards the inside surface of the bend, which reduces the tension in the struts, but also reduces the expanded diameter of the device.

In seeking procedural efficiency in this environment, clot retrieval devices with multiple bodies have often been preferred. Such devices can have an outer body capable of scaffolding a target vessel and an inner body for embedding and capturing a clot. These devices can perform well in engaging with and dislodging a clot but having a larger and often stiffer network of struts can potentially make it more difficult to retract the device and partially or fully collapse to re-sheath it within an outer catheter. Additionally, since these devices are designed so the clot is typically required to migrate radially inward through the outer member, the device can have a less firm grip on peripheral regions of a clot.

Additionally, conventional thrombectomy devices are usually aimed at removing either fibrin rich or soft clots. Currently, there is no way to identify whether a clot is fibrin rich or soft and friable (or some combination of the two) prior to the introduction of a thrombectomy device, preventing a user from knowing which device would improve the probability of a first pass success to reduce risk to the patient. Furthermore, clot heterogeneity can mean a clot can include fibrin rich cores in proximal, central, or distal portions of the overall clot anatomy, making a uniform and secure grip more difficult.

The challenges described above need to be overcome for any device to provide a high level of success in removing a clot of any type, restoring flow and facilitating good patient outcomes. The present designs are aimed at providing an improved clot retrieval device to address the above-stated deficiencies.

SUMMARY

The disclosed designs resolve these questions by providing a flexible dual-layer clot retrieval device in which the inner and outer members work in unison to capture and remove a clot. The designs can be intended for use as first pass devices with features that are just as effective at capturing fibrin rich and sticky clots as they are soft, friable clots.

The designs can feature a constrained delivery configuration and an expanded deployed configuration. The outer member can have wide opening struts to allow for clot integration into the device. Both the inner and outer members can be configured and shaped to pinch a clot in addition to embedding in it. In some examples, at least some portions of the devices are capable of folding and inverting proximally after engaging with a target clot to internalize and protect it. These actions can increase the security of the device's grip on a clot during all phases of retrieval, allowing safer and more efficient flow restoration.

The device can have a proximal tubular shaft for manipulation with a lumen extending therethrough. The shaft can be various sizes depending on the application. In one example, the shaft is a hypotube having an outer diameter of less than or equal to 0.021 inches. In another example, the shaft can have an outer diameter of approximately 0.026 inches. Distal of the shaft can be a framework of struts having a constrained delivery configuration, an expanded clot engaging deployed configuration when deployed at a target site, and an at least partially constrained clot pinching configuration.

In some examples, the framework of struts can form an elongate inner body and an outer cage. In one case, the inner body and outer cage can be laser cut from a single continuous hypotube. In another case, the proximal shaft, inner body, and outer cage can all be cut from the same continuous hypotube. The inner body can have a distal end, a longitudinal axis, and one or more clot pinching cells configured to pinch the clot when the device is transitioned from the deployed configuration to the clot pinching configuration. The outer cage can be arranged around the inner body, can extend from the distal end of the inner body, or be some combination of these. The outer cage can be expandable to a radial extent greater than the expanded inner body, or it can have the same or similar radial dimensions.

The clot pinching structure can take a variety of forms. The pinching structure can have a series of clot-receiving cells. The cells can consist of one or more flexible struts extending between crowns. The cells can have a horseshoe shaped saddle point at the proximal and distal ends of the cell so that the cells are capable of constricting portions of a clot in the cells when the struts are in radial compression. These patterns allows a microcatheter or outer catheter to be advanced over the proximal end of the pinching structure cells in order to compress and grip a clot between the tip of the catheter and at least a portion of the struts of the cells as the device is transitioned from the expanded deployed configuration to the partially-constrained clot pinching configuration. In another example, the clot pinching structure can be a flat pattern of struts arranged in an undulating or spiral fashion.

The properties of the inner body and outer cage can be tailored independently of each other. The outer cage can be coaxial with the inner body or can be radially offset. The inner body can be arranged substantially within the lumen of the outer cage.

In some examples, pull wires can extend through the lumen of the proximal tubular shaft and be fixedly connected to the outer cage at linkage points. The linkage points can be at least one of a crimp clamp, a weld, or a braid. A user manipulating the pull wires at the proximal end of the shaft can transition the outer cage from the expanded deployed configuration to an inverted clot housing configuration. During this transition, the pull wires can invert the outer cage so that at least part of it folds at transition points and back proximally over the inner body. The struts of the outer cage can thus enclose a clot and the inner body in the clot housing configuration. This inversion can internalize and contain both soft and firm portions of the clot for subsequent retraction and removal. In some cases, a remaining distal portion of the outer cage can also flare radially outward on activation of the pull wires to function as a fragment protection element during clot retrieval.

In some examples, the radial sizes of the inner body and outer cage can be heat set and varied depending on the application and the location of potential target occlusions within the vasculature. For targets in the neurovascular, the elongate inner body can have an outer diameter of approximately 2.25 mm in the expanded deployed configuration. Similarly, the outer cage can have an outer diameter of approximately 5 mm in the expanded deployed configuration and the inverted clot housing configuration.

Another design for the clot retrieval device can have a longitudinal axis, a proximal shaft, an inner body, an outer cage, and a tapered strut mesh connected to the distal end of the outer cage. The inner body, outer cage, and strut mesh can have a constrained delivery configuration, an expanded deployed configuration, and an at least partially constrained clot pinching configuration. After being deployed across a clot, the clot pinching configuration can be achieved by advancing a catheter over the proximal ends of the inner body and the outer cage until at least a portion of the clot is compressed between the tip of the catheter and at least a portion of the struts of the inner body, the outer cage, or a combination of the inner body and outer cage.

In some examples, the inner body can have struts forming a series of clot receiving cells. The cells can be heat set to extend in a generally sinusoidal wave pattern along the longitudinal axis in the expanded deployed configuration. In another example, the cells form a spiral pattern around the axis. In one case, the cells of the inner body are configured to embed with and stabilize a clot when expanded. In another case, the cells of the inner body can have at least one bend configured embed with and stabilize at least a portion of the clot. The inner body can be a range of radial sizes. In some examples, the inner body can have an outer diameter in the range of 1.25 mm-1.5 mm in the expanded deployed configuration.

The outer cage can have a series of segments extending in an axial fashion along the length of the device. Each segment can have one or more cells. In some examples, each segment can have two cells. Each cell of the outer cage can have a horseshoe shaped saddle point at the proximal and distal ends of the cell configured to compress and pinch at least a portion of the clot as the device is moved to the clot pinching configuration. The clot pinching configuration can be achieved by advancing a catheter over the proximal ends of the inner body and the outer cage until at least a portion of the clot is compressed between the tip of the catheter and at least a portion of the struts of the outer cage as the struts are radially compressed. Adjacent axial segments can be hingedly joined by a flexible connector strut, which can be the only point of contact between respective segments. The segments can therefore flex independently as the device is advanced or retracted through bends in the vasculature.

The outer cage can be various sizes depending on the target location within the vasculature. In one example, the outer cage can have an outer diameter of approximately 3 mm in the expanded deployed configuration. In another example, the outer cage can have an outer diameter of approximately 5 mm in the expanded deployed configuration.

The inner and outer bodies can share the same shaft and be coaxial around the longitudinal axis. At the proximal interface joint with the shaft, the outer cage can have a fully circumferential tubular outer collar circumscribing the shaft. The inner body can be formed laser cutting a tube with an outer diameter less than an inner diameter of the outer collar of the outer cage. The inner body can thus have a collar at the proximal interface that can slide within the outer collar.

A method for using the disclosed examples as first pass devices to extract both firm and soft clots from vessels can include a device having an inner body, an outer cage, and a proximal shaft. The inner body can be formed monolithically by laser cutting a tube, and have struts forming cells configured to embed with at least a portion a clot. In some cases, the outer cage can also be cut from the same continuous tube and extend distal to the inner body. In other cases, the outer cage can extend along the longitudinal axis around the inner body and be expandable to a radial extent greater than the inner body. The outer cage can also have struts forming cells configured to embed with at least a portion of the clot but also allow portions of the clot to migrate radially inward. The device can have a constrained delivery configuration, an expanded deployed configuration, and an at least partially constrained clot pinching configuration.

The method can include the step of delivering the device to a blood vessel adjacent to the site of a target clot. The clot composition can be firm, soft, or mixed with both firm and soft portions The device can be unsheathed to embed at least one of the cells of the outer cage and at least one of the cells of the inner body in the clot by expanding the device from the constrained delivery configuration to the expanded deployed configuration.

Another step can involve advancing an outer catheter distally so that the outer catheter engages with and impinges on the proximal ends of the inner body and outer cage to pinch in compression at least a firm portion of the clot with the cells of the inner body the outer cage. The outer catheter can be a microcatheter, access catheter, or another suitable outer sheath. The pinch can be maintained while the device is withdrawn so the grip on the clot is not lost.

In some examples, the cells of the inner body and/or outer cage can have struts forming bends or horseshoe shaped saddle points shaped to be compressed by the distal advancement of the outer catheter. The method can then further include the step of pinching at least a portion of the clot in a horseshoe shaped saddle point of at least one of the inner body cells when engaged with the outer catheter. Alternatively, or in addition to, the method can further include the step of pinching at least a portion of the clot in a horseshoe shaped saddle point of at least one of the outer cage cells when engaged with the outer catheter.

If the clot is frangible and not stiff enough to achieve a pinch, a user can feel the lack of tactile resistance when the shaft of the device is retracted, or the outer catheter is distally advanced. In this scenario, the outer catheter can be withdrawn, and the device can be redeployed to the expanded configuration to imbed the clot. In some examples, struts of the outer cage can be inverted back over the device, and the method can involve the step of inverting the struts proximally to internalize the clot and the inner body. The inner body can be held in position while the outer cage struts are inverted so the clot is not pushed proximally.

When the firm and/or soft clot has been captured by the device, the method can involve the step of removing the clot retrieval device and the captured clot from the patient. This can be done, for example, by retrieving the device proximally into a guide catheter using aspiration. If a firm portion of the clot can be pinched, the pinch can be maintained during this step so the grip on the clot is not lost. Additionally, if the struts of the outer cage have been inverted proximally (using tensioned pull wires or other method) to internalize and help secure the clot, this configuration can also be maintained.

After retrieving some or all of the occlusive clot, an assessment can be made to the degree to which the vessel is patent. Additional passes with the clot retrieval device can be made if an obstruction remains in the vessel. Any remaining devices can then be removed from the patient once adequate recanalization of the target vessel is observed. The devices of the present disclosure, however, provide a means to minimize the number of catheter advancements required to treat a patient, thereby reducing the likelihood of vessel damage and the associated risk of vessel dissection in cases where multiple passes are required.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with reference to the following description in conjunction with the accompanying drawings, where like reference numbers indicate elements which are functionally similar or identical. The drawings are not necessarily to scale, emphasis instead being placed upon illustrating principles of the invention. The figures depict one or more implementations of the inventive devices, by way of example only, not by way of limitation.

FIG. 1 is a view of a clot retrieval device according to aspects of the present invention;

FIG. 2 shows the clot retrieval device of FIG. 1 with the struts of the outer cage inverted proximally using pull wires according to aspects of the present invention;

FIGS. 4A-4B demonstrate a method of use for a clot retrieval device for capturing a soft clot according to aspects of the present invention;

FIGS. 5A-5B depicts the continuation of the method steps in FIGS. 4A-4B according to aspects of the present invention;

DETAILED DESCRIPTION

Figure 3A:
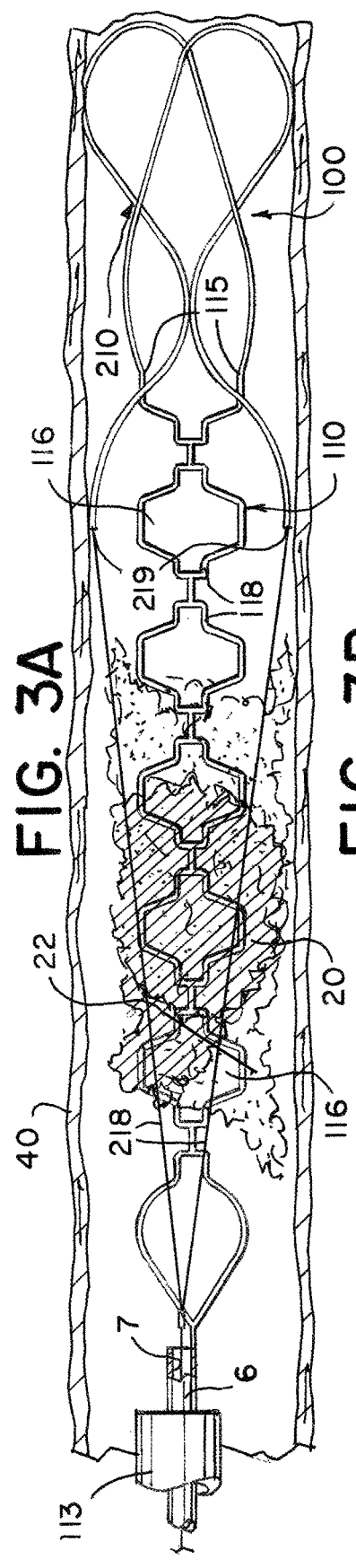
FIGS. 3A-3C illustrate a method of use for a clot retrieval device for capturing a clot having both soft and firm components according to aspects of the present invention.

The objective of the disclosed designs is to create a clot retrieval device capable of providing more effective and efficient removal of clots of various composition in the vasculature while maintaining a high level of deliverability and flexibility during procedures. The designs can be first pass clot retrieval devices that can be used to the removal of any clot type, whether they be firm and sticky, soft and friable, or a combination of the two.

The designs can have an outer expandable cage within which runs an inner expandable body. The inner body and outer cage can have large openings where a radial force allows portions of the clot to migrate into the openings. The cells of one or both of the inner body and outer cage can have features configured to pinch at least a portion of the clot when an outer catheter is advanced distally upon the device. These pinching designs increase the grip security of the clot retrieval device. The devices can also be configured so that at least a portion of the device can invert proximally to internalize and protect the clot during retrieval.

Both the inner and outer expandable members are desirably made from a material capable of recovering its shape automatically once released from a highly strained delivery configuration. A suitable manufacturing process can be to laser cut a Nitinol tube and then heat set and electropolish the resultant structure to create a framework of struts and connecting elements. A range of designs are envisaged for each of these elements as described, and it is intended that any of these elements can be used in conjunction with any other element, although to avoid repetition they are not shown in every possible combination.

Accessing the various vessels within the vascular to reach a clot, whether they are coronary, pulmonary, or cerebral, involves well-known procedural steps and the use of a number of conventional, commercially available accessory products. These products are well understood and widely used in laboratory and medical procedures. When these or similar products are employed in conjunction with the disclosure of this invention in the description below, their function and exact constitution are not described in detail.

Specific examples of the present invention are now described in detail with reference to the Figures. While the description is in many cases in the context of mechanical thrombectomy treatments, the designs may be adapted for other procedures and in other body passageways as well.

Figures 1, 2:
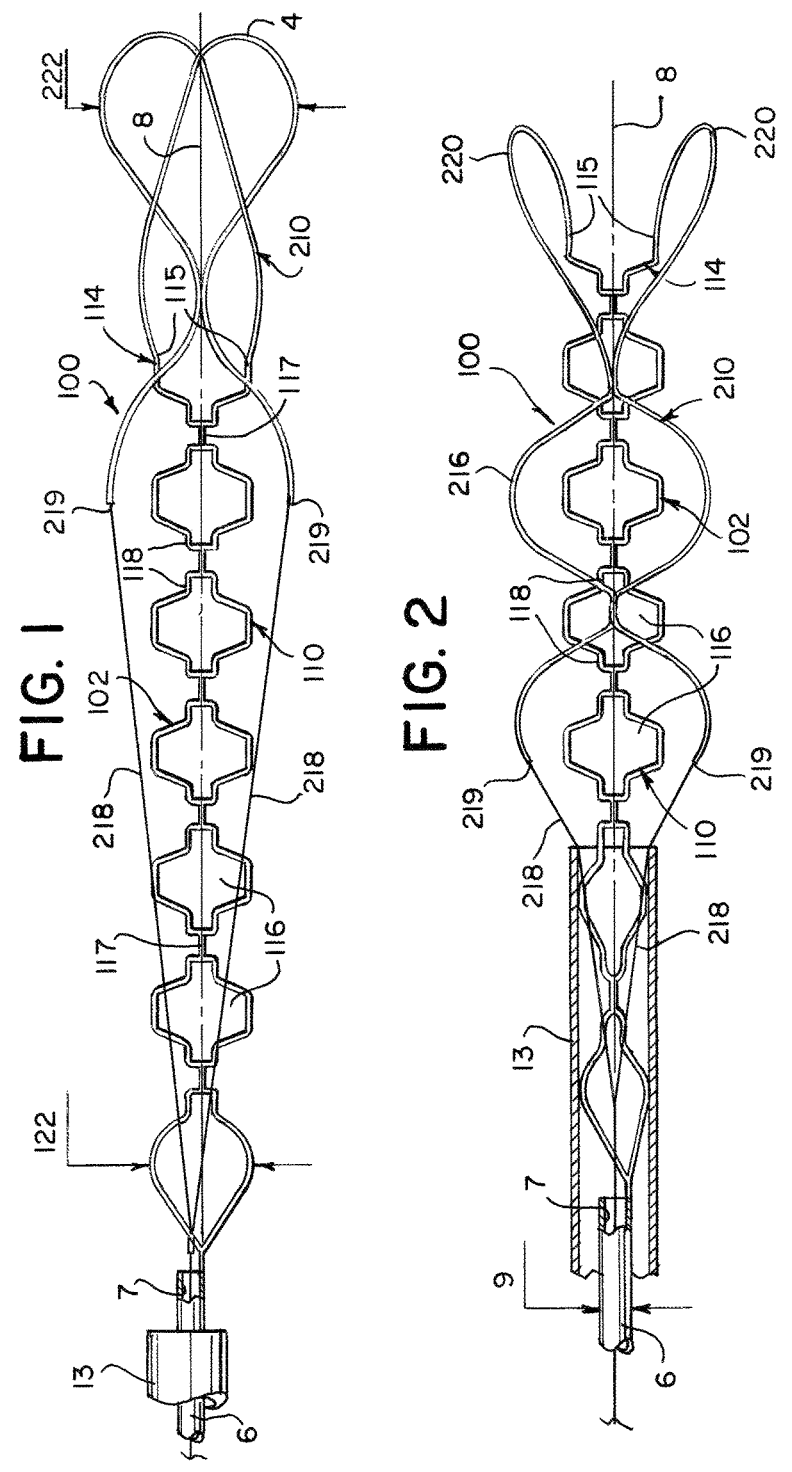

Referring to FIG. 1, a clot retrieval device 100 can have an elongate shaft 6 from which distally extends a strut framework 102 with an inner body 110 and an outer cage 210 expandable from a collapsed or constrained delivery configuration to an expanded deployed configuration at the target site of a vessel occlusion or clot. The delivery method can be through, for example, a microcatheter 13 or other outer catheter or sheath depending on the access requirements of the target location. Upon being exposed beyond the distal end of the microcatheter 13, the device 100 can self-expand to the deployed configuration depicted in FIG. 1. The occlusion is typically a thrombus (blood clot) impeding blood flow in the vessel. Having a configuration with both an inner body 110 and outer cage 210 allows the clot to be retained inside the device which can minimize the risk of vessel damage during removal.

The inner body 110 can be a network of struts forming an axial series of cells 116. The struts of the cells 116 can have a high radial force when expanded to assist with interpenetrating and embedding the cells within the clot. The proximal and distal end of each cell can taper into substantially a "U" or horseshoe shaped saddle points 118. This shape of the saddle points 118 allows the cells 116 to contract radially when the microcatheter 13, or another outer catheter, is advanced over the proximal end of the device. This contraction can pinch a firm portion of a clot embedded within the cell or cells.

Having multiple pinching cells 116 can be beneficial for capturing clots which have fibrin cores in the proximal, center, and/or distal locations within the clot. The cells can grip the clot tightly as the device is retracted into the outer catheter until resistance is felt, indicating a pinch grip that can be further secured with aspiration.

The pinch facilitates removal of the clot by increasing the grip of the device on the clot, particularly in the case of substantially fibrin rich clots. The pinch can also elongate the clot, thereby reducing the dislodgement force by pulling the clot away from the vessel wall during the dislodgement process. Retention of the clot can be improved during retraction to the microcatheter or outer catheter by controlling the proximal end of the clot and preventing it from snagging on a side branch vessel.

The ends of adjacent cells 116 can be connected by flexible connecting struts 117. The connecting struts 117 can act as a hinge between cells and can be the only point of contact between adjacent cells. As a result, the individual cells can flex independently as the device is advanced or retracted through bends in the vasculature and can respond locally to the forces exerted on the device by a captured clot.

The outer cage 210 can be fixedly connected to the distal end 114 of the inner body 110. The gently curved loops of the outer cage 210 can give the device 100 an atraumatic profile near the distal end 4. In some examples, the inner body 110 and outer cage 210 can be formed monolithically, whereby the struts of the inner body transition to become struts of, and take on the shape of, the outer body. This is illustrated in FIG. 1 where transition points 115 at the distal end 114 of the inner body 110 make the transition to the broadly looped structure of the outer body 210. Cutting and heat setting the inner body 110 and outer cage 210 from the same tube can simplify the manufacturing process and remove potential kink points from stiffness gradients in the device.

The struts of the outer cage 210 can be very flexible with low radial force to allow the struts to be manipulated by pull wires 218 or other suitable actuation method to change the shape of the outer cage as desired. The flexibility of the struts also allows the outer cage 210 to be collapsed to the outer diameter 122 of the inner body 110 for navigation through narrower vessels.

The inner body 110 and outer cage 210 can be preferably made of a super-elastic or pseudo-elastic material such as Nitinol or other such alloy with a high recoverable strain and suitably high modulus and tensile strength. An advantage of using self-expanding bodies with these materials is that because of the volumetric properties and stiffness of a target clot, resistance can cause the device 100 to initially expand to only a fraction of its freely expanded diameter when deployed across the clot. This gives the outer body 210 the capacity to further expand to a larger diameter while being retracted so that it can appose vessel walls as it is retracted into progressively larger and more proximal vessels In one example, the inner body 110 and outer cage 210 can be laser cut from a single continuous pieces of tubing which also serves as the shaft 6. Having a shaft 6 which doubles as a tube can allow the lumen 7 of the shaft tube to be used as a conduit for pull wires 218 or other actuation members or devices as necessary.

The tubing can be in raw material form, for example a Nitinol hypotube so that the struts of the inner body 110 and outer cage 210 can be laser cut and heat set to the desired shapes and dimensions. For example, the inner body 110 can be heat set to have an outer diameter 122 of approximately 2.25 mm when expanded to the deployed configuration. Similarly, in the same deployed configuration the outer cage 210 can be heat set to have an outer diameter 222 of approximately 5.00 mm. The device can thus be effectively spring loaded within a microcatheter and expand to these dimensions when deployed at the target site.

The radial size of the outer cage 210 can allow it to remain in contact with and appose the vessel walls as well as protecting against distal migration of the clot as the device is retracted proximally into progressively larger diameter vessels. Apposition with the vessel walls can also reduce the axial force necessary to initially dislodge a clot from the vessel.

FIG. 2 shows an example configuration for the device 100 of FIG. 1 after the capture of a clot (not shown). The cells 116 of the inner body 110 can serve as inlets to stabilize the clot and allow the device, when retracted, to apply a force to the clot in a direction substantially parallel to the direction in which the clot is to be pulled from the vessel (i.e. substantially parallel to the longitudinal axis 8). This also means that any outward radial force applied to the vasculature by the outer cage 210 can be kept to a minimum.

When the cells 116 of the inner body 110 have been embedded within a clot, the pull wires 218 can be tensioned and retracted to invert the flexible struts of the outer cage 210 proximally as shown to internalize the inner body and clot. The pull wires 218 can be retrieved using a handle positioned at the proximal end of the device shaft. The wires 218 can pull the larger diameter outer cage 210 while the inner body 110 is left in position so that a pinch can be maintained between the saddle points 118 of the inner body cells 116, microcatheter 13, and at least a firm portion of the clot as described.

When inverted, the outer cage 210 can feature a series of broad loop segments 216 disposed around the longitudinal axis 8 and inner body 110. At the inner body distal end 114, the inner body/outer cage transition points 115 can form distal crowns 220 to act as a fragment protection element during clot removal to prevent the distal migration of debris. The crowns 220 can also have a flared diameter similar to that of the target vessel so that it can help to securely capture fragments from friable parts of the clot.

The shaft 6 can be a stock tubing size chosen to be compatible with commonly available delivery sheaths. In one example, the outer diameter 9 of the shaft 6 can be less than approximately 0.021 inches to ensure compatibility with a 0.021 inch inner diameter microcatheter. In another example, the shaft 6 can have a slightly larger outer diameter of approximately 0.026 inches to be compatible with 0.027 inch inner diameter microcatheter.

The shaft 6 and other portions of the device 100 can also have indicator bands or markers (not shown) to indicate to the user when the distal end of the device is approaching the end of the microcatheter during insertion or mark the terminal ends of the device during a procedure. These indicator bands can be formed by printing, removing, or masking areas of the shaft for coating, or a radiopaque element visible under fluoroscopy, so that they are visually differentiated from the remainder of the shaft.

The shaft 6 can also be coated with a material or have a polymeric jacket to reduce friction and thrombogenicity. The coating or jacket may consist of a polymer, a low friction lubricant such as silicon, or a hydrophilic/hydrophobic coating. This coating can also be applied to some or all of the outer cage 210 and inner body 110.

Figure 3B:
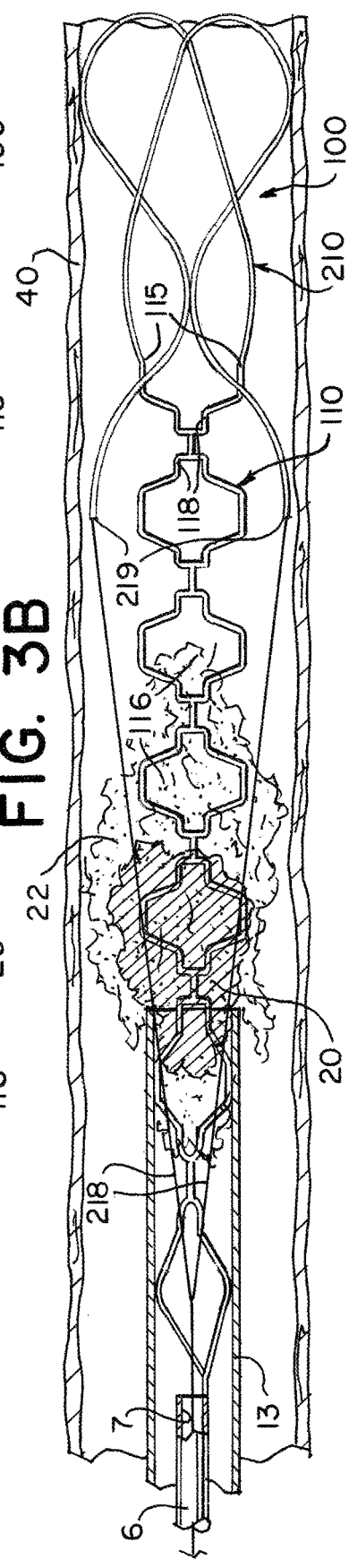
Figure 3C:
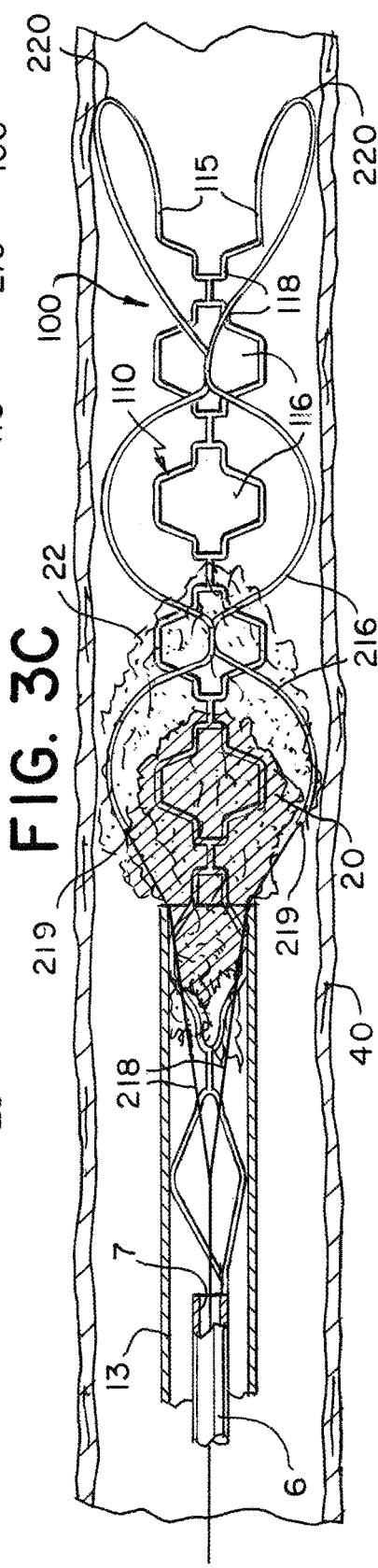

FIGS. 3A-3C illustrate a method for using the device 100 in the vasculature 40 to capture a non-homogenous clot 20, 22 with both firm and soft components. In FIG. 3A, the device can be deployed from a microcatheter 13 in a clot with the cells 116 of the inner body 110 section exposed to the clot. The microcatheter 13 can then be advanced distally to re-sheath at least a portion of the cells 116 of the inner body 110 and the pull wires 218. Alternatively, another outer catheter or sheath can be used. The saddle points 118 can form a natural inflection point for the cells 116 to fold down radially. If a fibrin rich portion 20 of the clot is present, the cells 116 can achieve a pinch on this section of the clot between the inner body 110 and microcatheter, as shown in FIG. 3B.

Once a pinch is achieved and the user feels the resulting resistance, the pull wires 218 can be retracted through the shaft 6. The wires pull the larger diameter heat set portion of the outer cage 210 proximally at linkage points 219 while leaving the inner body 110 in position to maintain the pinch. The retrieval of the pull wires 218 withdraws the loop segments 216 of the outer cage 210 over both the firm portions 20 and soft portions 22 of the clot to internalize the entire clot within the outer cage, as depicted in FIG. 3C. The full device can then be withdrawn with the clot into a guide catheter or other outer sheath.

The bond between the pull wires 218 and struts of the outer cage 210 at the linkage points 219 can be by a number of methods. In some examples, a mechanical connection such as a crimp, braid, or bulb/eyelet combination can be utilized. In other cases, a thermal process such as a weld or braze can be used.

Figure 5B:
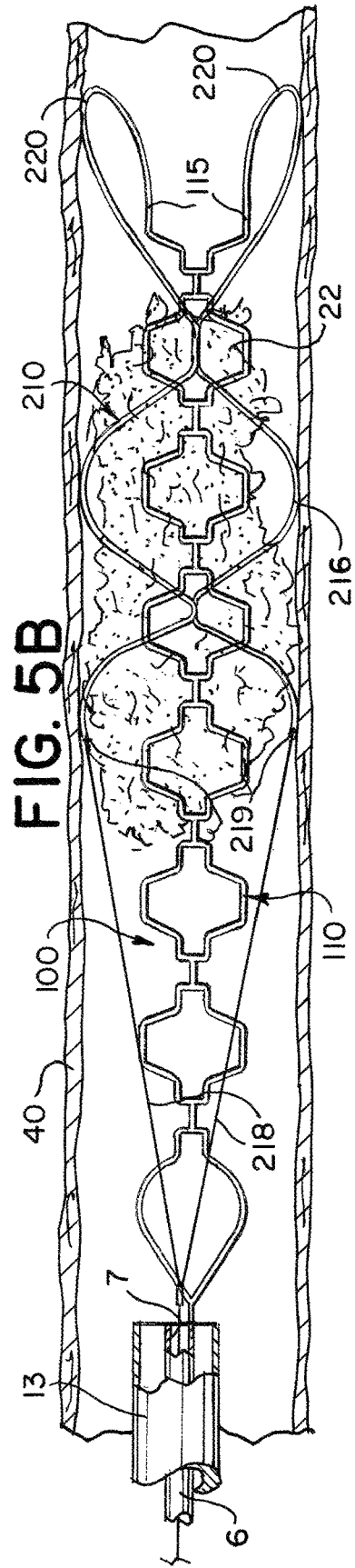

FIGS. 4A-4B and FIGS. 5A-5B demonstrate a method for using the device if only a soft clot 22 is present. The device can be deployed in the clot 22 so that the cells 116 of the inner body 110 can be exposed to and embed in the clot as shown in FIG. 4A. In FIG. 4B, the microcatheter 13 can be advanced distally to re-sheath at least a portion of the cells 116 of the inner body 110 and the pull wires 218 to attempt to pinch the clot as seen in FIG. 4B. If the user does not feel the resistance of a pinch between the inner body 110 and microcatheter, it suggests the clot 22 is soft (no fibrin rich portion or portions). The device can then be redeployed out of the microcatheter 13 to embed the inner body 110 and stabilize the clot (FIG. 5A). The user can then tension the pull wires 218 and draw them proximally to invert the outer cage 210 while leaving the inner body 110 in position to internalize the soft clot 22 (FIG. 5B). The crowns 220 can prevent distal migration of clot fragments while the full device and clot is withdrawn into the guide catheter.

Figure 6:
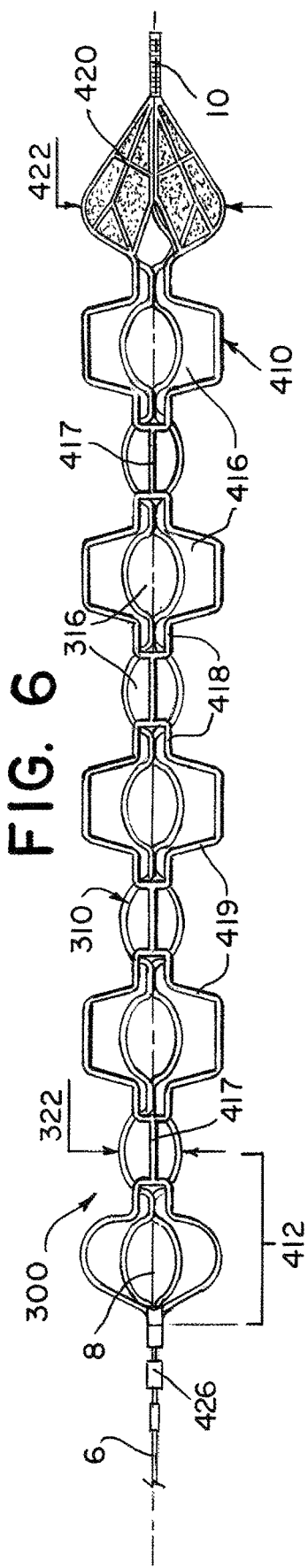
FIG. 6 is a plan view of another example of a clot retrieval device according to aspects of the present invention.

Another example of a clot retrieval device 300 capable of being a first pass device for capturing both firm and soft clots is seen in the plan view in FIG. 6. The device 300 can have a constrained delivery configuration for delivery through a microcatheter, an expanded deployed configuration, and an at least partially constrained clot pinching configuration for gripping firm or fibrin rich clots. The device 300 can have a longitudinal axis 8, a proximal shaft 6, and an expandable structure of struts forming an inner body 310 and an outer cage 410. Similar to other designs, the inner body 310 and outer cage 410 can be cut from a shape memory alloy such as Nitinol to allow the struts to be heat set to desired shapes when expanded. The inner body 310 and outer cage 410 can help to retain the clot inside the device to reduce the risk of damage to the vessel wall during retrieval as the clot is not brushed against the vessel wall for grip.

The inner body 310 can be configured to stabilize a clot during the removal process and add support and additional grip for particularly soft clots. The inner body 310 can be a low profile series of clot engaging cells designed with an "s-wave" or sinusoidal wave final heat set shape. The low profile design allows more clot reception space between the inner body 310 and outer cage 410 to minimize clot shearing when the device is retrieved back into an intermediate catheter or other outer catheter. In one example, the inner body 310 can have an expanded outer diameter in a range of approximately 1.25-1.5 mm. In other examples, the inner body can have an expanded diameter determined by the difference in foreshortening when the inner body and outer cage are crimped together into a microcatheter for delivery to a target site.

Figure 7:
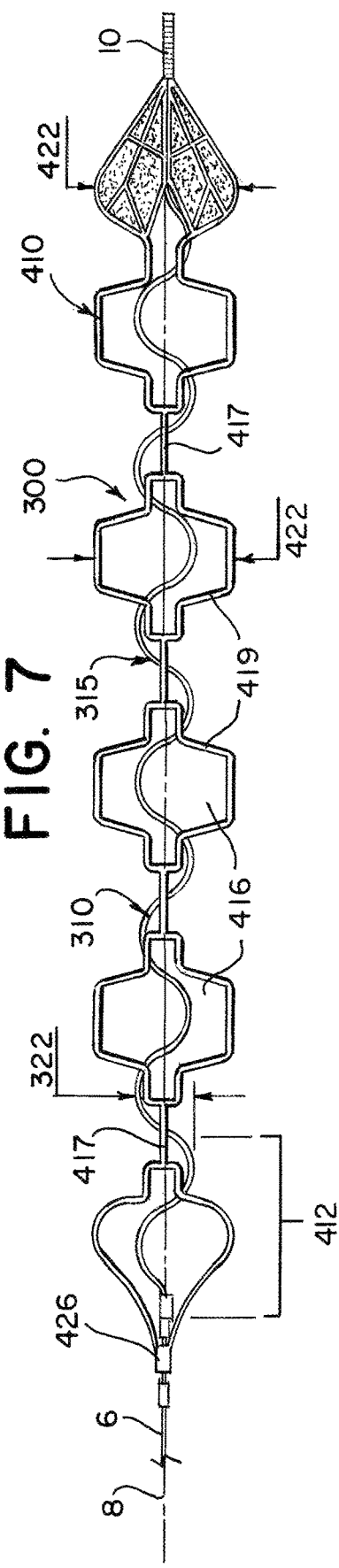
FIG. 7 is an elevation view of the clot retrieval device of FIG. 6 according to aspects of the present invention.

An elevation side view of the device 300 from FIG. 6 is depicted in FIG. 7. The outer cage 410 can have an axial series of body segments 412 disposed around the inner body 310 and heat set with a substantially larger outer diameter 422 than the inner diameter 322 of the inner body. In some preferred examples this outer diameter 422 can be approximately 5 mm. Each segment 412 can have one or more cells 416 with horseshoe shaped saddle points 418 at the proximal and distal ends of each cell.

The device 300 shown in FIGS. 6-7, for example, has two cells 416 per segment 412 around the longitudinal axis 8 perpendicular to each other. Note that due to the perpendicular nature of the cells 416 from the plan and elevation views as shown in FIG. 6 and FIG. 7, respectively, each cell of the body segments 412 can have 180 degrees of curvature where a flexible connector strut 417 serves as the top/bottom of the adjacent cell when the device 300 is rotated 90 degrees. The result can thus be a cylindrical shape for the outer cage 410 around the longitudinal axis 8.

Expansion of the outer cage 410 can cause compression and/or displacement of the clot during the expansion, depending on the level of scaffolding support provided by the struts. When an expandable body provides a high level of scaffolding the clot can be compressed. Alternately, when an expandable body provides an escape path or opening the expanding body urges the clot towards the opening. The clot itself can have many degrees of freedom and can move in a variety of different directions. When the device is sufficiently long, many of the degrees of movement freedom available to the clot are removed. This allows the clot to be retrieved without being excessively compressed. This is advantageous because compression of clot can cause it to dehydrate, which in turn increases the frictional properties and stiffness, which make the clot more difficult to disengage and remove from the vessel. This compression can be avoided if the clot can easily migrate inward through the cells of the outer cage.

As a result, the cells 416 from the device 300 shown in FIGS. 6 and 7 can have wide opening struts to allow a clot to migrate radially through the outer cage 410 once deployed in a clot. Similar to other examples, distally advancing a microcatheter or other catheter after deployment can compress the saddle points 418 of each cell 416 to pinch fibrin rich portions of a clot for a secure grip during removal.

Adjacent segments 412 of the outer cage 410 can be joined by a flexible connector strut 417. As the saddle points 418 taper the ends of the cells 416 of each segment 412 to a point, a single connector strut 417 can be the only point of contact between respective segments. This allows segments to hinge about the connector struts to improve device flexibility and vessel wall apposition. The connector struts can also allow the cells 416 of individual segments to open locally to an increasing diameter to maintain a good grip on a clot between the inner body 310 and outer cage 410. The ability to locally increase to a larger diameter can be especially useful in situations where some or all of a target clot is located in difficult anatomy, such as a bifurcation, allowing the clot to be retained inside the vessel.

The outer cage 410 can also have a final segment with a tapered mesh end 420 for preventing small fragments from breaking away from the main clot and re-occluding in smaller, more distal vessels. The mesh end 420 can also help to protect against sections of the clot which detach as they roll over or change shape during retrieval. The distal struts forming this segment 420 can be bulged or flared so the distal end of the outer cage 410 is rendered atraumatic to the vessels in which it is used. The tapering and convergence of these struts can also reduce the pore size of the mesh to create an effective fragment capture zone.

Figure 8:
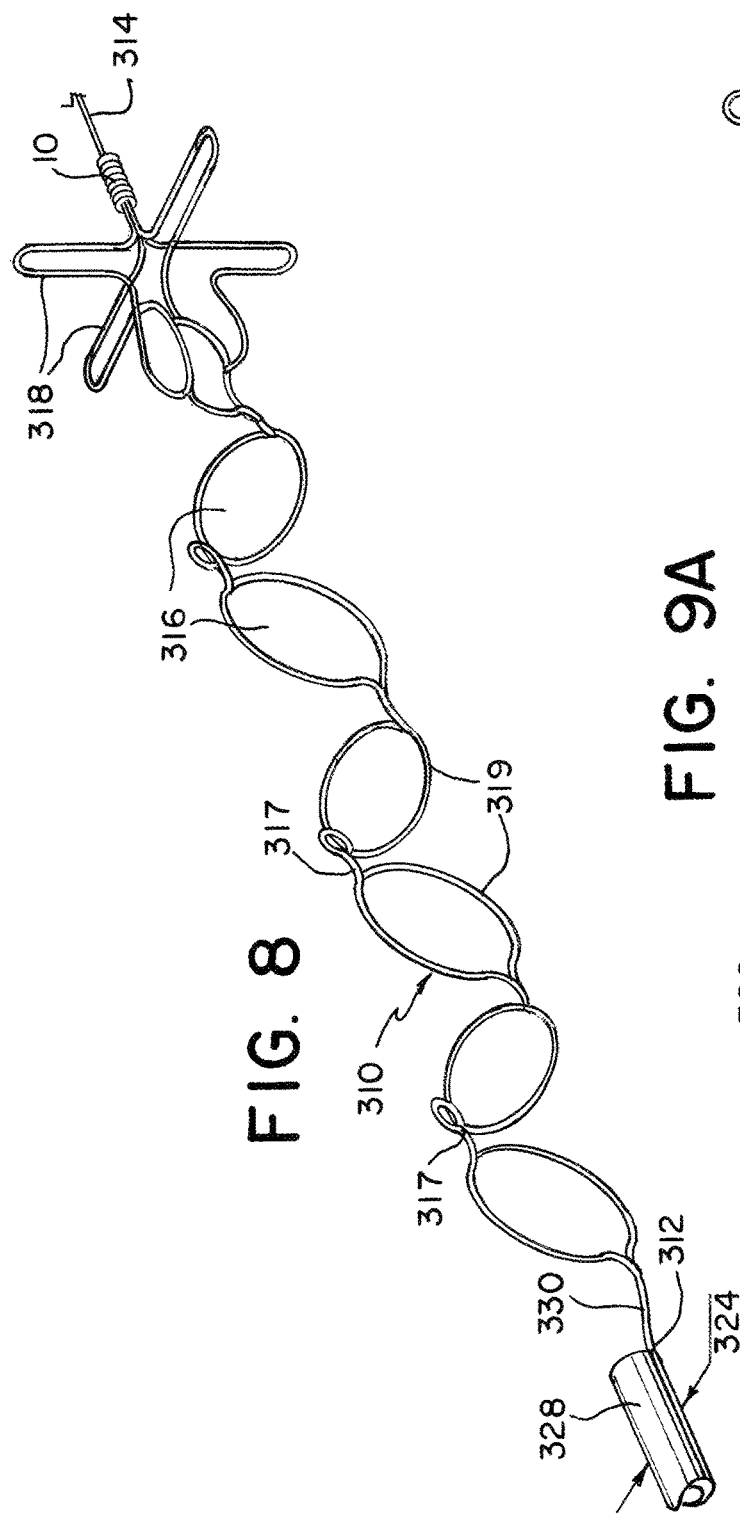
FIG. 8 shows a perspective view of the inner body of the clot retrieval device of FIG. 6 according to aspects of the present invention.

A perspective view of the inner body 310 of the device 300 from FIG. 6 and FIG. 7 is illustrated in FIG. 8. The sinusoidal waveform design of the body cells 316 is visible as the struts contain bends 319 between amplitude peaks 317 of the pattern. The bends 319 of the cells 316 can bias movement away from, or at least not in the same direction as, the clot pinching cells 416 of the outer cage 410 so that the inner body 310 stabilizes but does not shear portions of the clot when the proximal portion of the device is partially constrained in the clot pinching configuration. The bends or crowns can also help to provide a better grip on the clot by embedding with and balancing the clot for the critical initial step of disengaging it from the vessel, enabling the outer cage 410 to be configured with a lower radial force.

The cells 316 and waveform shape of the inner body 310 allow the device to accommodate minor length differentials through stretching without the application of significant tensile or compressive forces to the joints. Length differentials can occur when, for example, the device is expanded, collapsed or deployed in a small vessel. The waveform arrangement of the struts of the inner body cells 316 also allows the cells to lengthen and shorten enough so that the lengths of the inner body 310 and outer cage 410 can be substantially the same when loaded in a microcatheter and when freely expanded at the target site. However, the cells can still have sufficient structural rigidity so the device 300 can be advanced or retracted without excessively lengthening or shortening the inner body 310 and outer cage 410.

The inner body 310 can also transition distally from the single cell sinusoid pattern into a collection of radially expanded struts 318. In the example shown, four expanded struts 318 can be positioned spaced equally 90 degrees around the longitudinal axis. The flared or expanded struts can aid the distal mesh fragment segment 420 of the outer cage 410. The expanded struts can also align the foreshortening of the inner body 310 and outer cage 410 during the crimping of the device into an insertion tool or microcatheter.

Figure 9A:
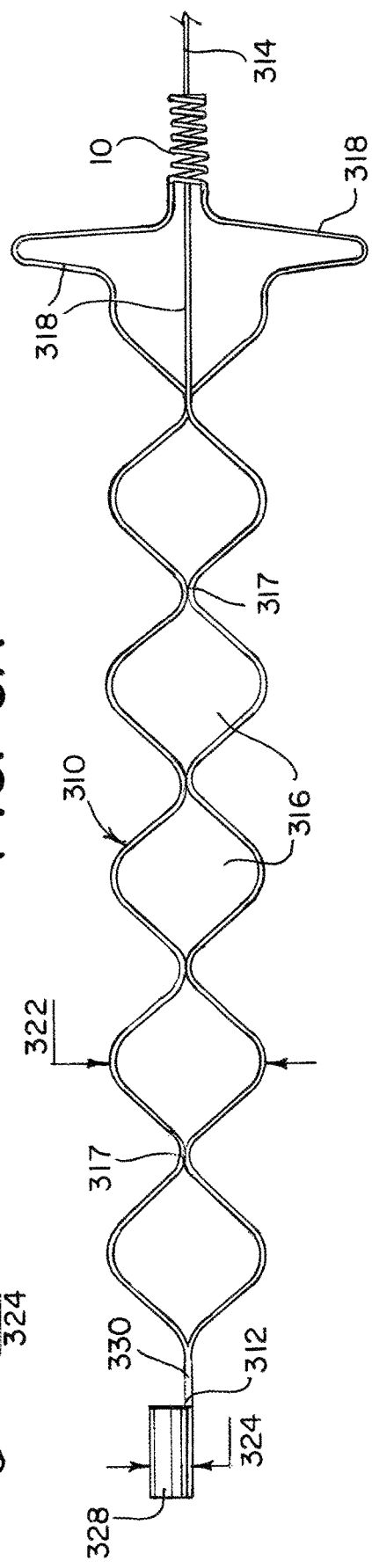
FIG. 9*a* illustrates a plan view of the inner body of FIG. 6 according to aspects of the present invention.
Figure 9B:
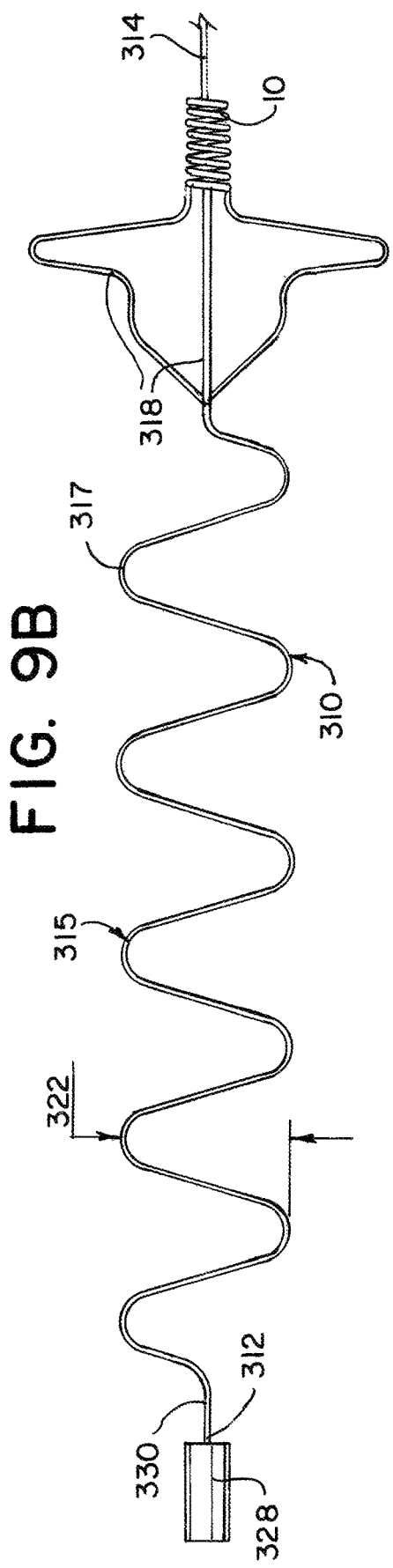
FIG. 9*b* depicts an elevation view of the inner body of FIG. 6 according to aspects of the present invention.

FIGS. 9A and 9B provide a top view and side view, respectively, of the inner body 310 of FIG. 8 independent of the outer cage 410 of the device 300. FIG. 9A shows the sequence of cell openings 316 in the inner body 310. Each wave can have a single cell opening 316. The cells can have a diameter of approximately 1.25-1.5 mm or can have a slightly different diameter determined by the difference in the foreshortening of the inner body 310 and outer cage 410 during crimping of the device into an insertion tool or microcatheter. The expanded struts 318 near the distal end 314 can be a larger outer diameter (much closer to the expanded outer diameter of the outer cage) than the cells 316 of the inner body 310, and as a result these struts can also make up a significant amount of the take-up length required between the inner body and outer cage.

FIG. 9B illustrates a side view of FIG. 9A clearly showing the sinusoidal wave pattern 315 of the cells 316 of the inner body 310. The most proximal cell of the pattern can terminate in a connecting strut 330 linking it to a partially circumferential inner collar 328 at the proximal end 312 of the inner body. The struts of the inner body can be formed monolithically with the collar 328 by cutting and machining a single hypotube with an outer diameter 324 equal to that of the collar. At the distal end 314 of the inner body 310 can be a radiopaque coil 310 or marker band to mark the terminal end of the device during a procedure.

Figure 10:
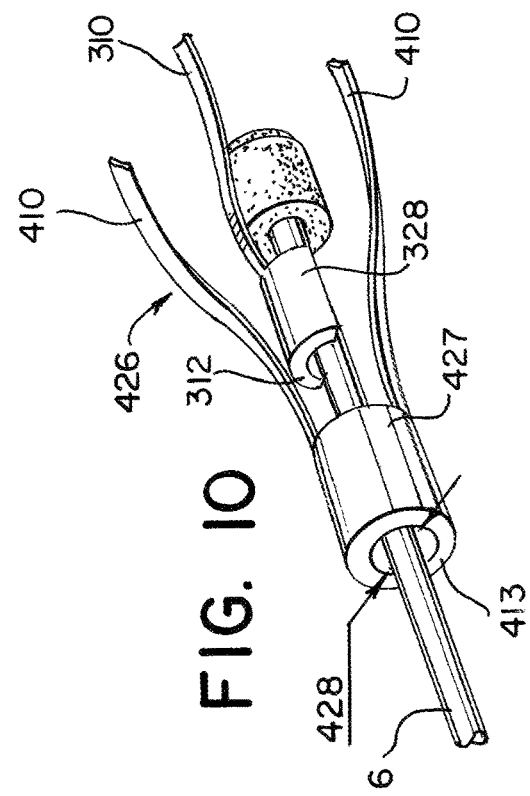
FIG. 10 is a view of an example proximal joint for the clot retrieval device of FIG. 6 according to aspects of the present invention.

The proximal connections of the inner body 310 and outer cage 410 to the elongate shaft 6 can be constructed so the inner body and outer cage can have some small amount of independent translation with respect to each other. The translation can be, for example, a linear translation along an axis, a rotation of one body with respect to the other, or some combination of these. An example of a joint where this can be accomplished with a collar assembly 426 is illustrated in the exploded view in FIG. 10. The proximal end 413 of the outer cage 410 can have a tubular collar 427 circumscribing the elongate shaft 6. The proximal end 312 of the inner body 310 can have the partially circumferential inner collar 328 riding on elongate shaft 6 as mentioned above. The partially circumferential inner collar 328 can be cut from a hypotube having an outer diameter 324 less than the inner diameter 428 of the tubular collar 427 of the outer cage 410. Such a configuration can allow the inner collar 328 to sit radially inboard of the tubular outer collar 427 so that a small amount of rotation of either the inner body 310 or outer cage 410 can be possible with respect to the other. A partially circumferential setup also allows the inner collar 328 to be assembled on the shaft 6 with a fully circumferential outer collar 427.

The coaxial collar assembly 426 of the partial inner collar 328 of the inner body 310 and outer collar 427 of the outer cage 410 can allow for the two bodies to be substantially aligned with the neutral axis of the device 300 during bending within the vasculature. The rotation potential between the outer cage 410 and inner body 310 allowed by the collar assembly 426 can also help to prevent clot shearing which could otherwise occur with a static and fixed connection.

Figure 11:
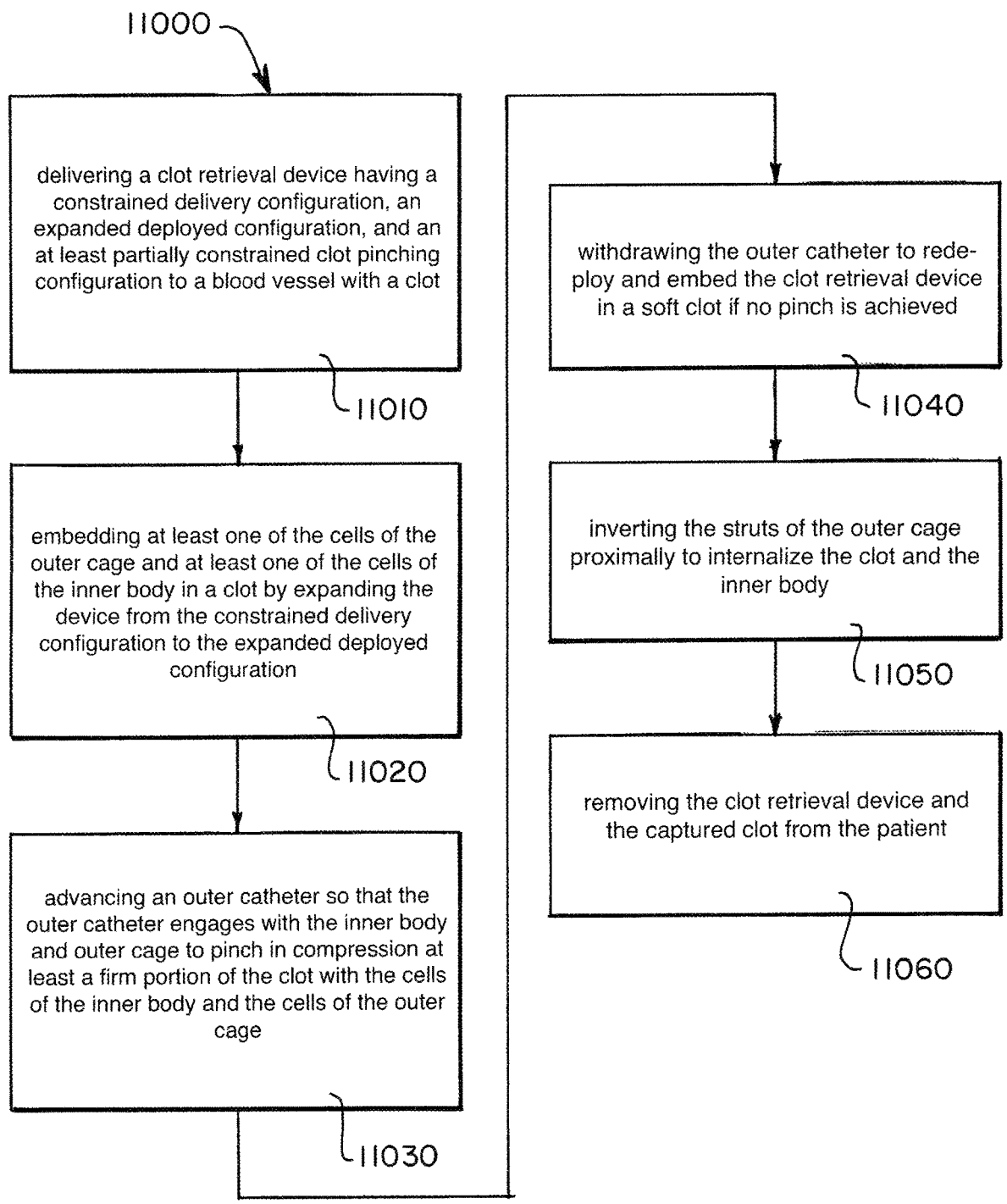
FIG. 11 is a flow diagram outlining a method of use for a clot retrieval device according to aspects of the present invention.

FIG. 11 diagrams method steps for performing a thrombectomy procedure with such a device. The method steps can be implemented by any of the example devices or suitable alternatives described herein and known to one of ordinary skill in the art. The method can have some or all of the steps described, and in many cases, steps can be performed in a different order than as disclosed below.

Referring to a method 11000 outlined in FIG. 11, step 11010 can involve delivering a clot retrieval device across a target clot of unknown composition. The clot can be firm and fibrin rich, soft and friable, or some combination of the two. The clot retrieval device can be delivered through a microcatheter or other suitable delivery catheter and have a collapsed configuration during delivery and an expanded deployed configuration when the delivery catheter is retracted. An elongate shaft can be used to manipulate the device by a user.

An expandable element of struts can be attached to the distal end of the elongate shaft and have an outer cage of cells and an inner body of cells within the lumen of the outer cage. Step 11020 can involve embedding at least one of the cells of the outer cage and at least one of the cells of the inner body in a clot by expanding the device from the constrained delivery configuration to the expanded deployed configuration. The radial force from the expansion of the outer cage can cause at least a portion of the clot to migrate radially inward.

In step 11030, a microcatheter or other outer catheter can be advanced distally to engage with at least some of the cells of the inner body and outer cage to pinch in compression at least a firm portion of the clot. The cells of the inner body and/or outer cage can be shaped to have bends at the axial apices shaped to fold the cell down radially as the device is partially re-sheathed. The saddle points can therefore exert a firm grip on any fibrin rich cores in the clot composition.

The distal advancement of the outer catheter can continue until resistance is felt by the user, indicating a pinch has been achieved, or no resistance is felt indicating the lack of fibrin rich portions of the clot. If no pinch is achieved, step 11040 can involve withdrawing the outer catheter to redeploy and embed the device in the clot. This redeployment stabilizes the soft clot within the cells of the device.

In step 11050, some or all of the struts of the outer cage can be inverted proximally to fold back over and internalize the clot and inner body. The inversion can protect the clot and reduce possible interactions or snags due to friction, bifurcations, and/or sharp bends in the vasculature. The struts can be pulled proximally by the user utilizing pull wires that are retracted and run through an inner lumen of the device shaft or by other suitable means. For example, the pull wires can extend through a hypotube device shaft and be actuated from a handle positioned on the proximal end of the shaft. In addition, the proximal joint of the inner body, outer cage, and the elongate shaft can be configured to allow some relative motion between them, reducing retraction forces and the risks of clot shearing.

Step 11060 can involve removing the clot retrieval device and captured clot from the patient. This can be accomplished, for example, by retrieving the device into an outer catheter with the aid of aspiration. If a pinch was achieved, it can be maintained by keeping the relative positions of the device and outer catheter during withdrawal. If required, the device may be rinsed in saline and gently cleaned before being reloaded into the microcatheter to be reintroduced into the vasculature when there are additional segments of occlusive clot, or if further passes for complete recanalization are needed.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology. For clarity and conciseness, not all possible combinations have been listed, and such variants are often apparent to those of skill in the art and are intended to be within the scope of the claims which follow.

What is claimed is:

1. A device for removing a clot from a blood vessel, comprising:
    a proximal tubular shaft comprising a lumen extending therethrough;
    a framework of struts having a constrained delivery configuration, an expanded clot engaging deployed configuration, and an at least partially constrained clot pinching configuration, the framework of struts comprising:
        an elongate inner body comprising a distal end, a longitudinal axis, and one or more clot pinching cells configured to pinch the clot on movement from the deployed configuration to the clot pinching configuration; and
        an outer cage connected to the distal end of the elongate inner body and expandable to a radial extent greater than the elongate inner body; and
    one or more pull wires extending through the lumen of the proximal tubular shaft and fixedly connected to the outer cage, the one or more pull wires configured to move the outer cage from the expanded deployed configuration to an inverted clot housing configuration,
    wherein each of the one or more clot pinching cells are arranged in an axial series and are hingedly joined to each of their respective adjacent clot pinching cells of the one or more clot pinching cells by a flexible connector strut, the flexible connector strut being the only point of contact between the respective adjacent clot pinching cells of the one or more clot pinching cells.

2. The device of claim 1, wherein the elongate inner body and outer cage are monolithically formed through laser cutting a single continuous tube.

3. The device of claim 1, wherein each clot pinching cell of the one or more clot pinching cells comprise a horseshoe shaped saddle point at proximal and distal ends of the clot pinching cell.

4. The device of claim 1, wherein the one or more pull wires are connected to the outer cage at a linkage point by at least one of a crimp clamp, a weld, or a braid.

5. The device of claim 1, wherein the struts of the outer cage are configured to invert proximally when the outer cage is moved from the expanded deployed configuration to the inverted clot housing configuration.

6. The device of claim 5, wherein the struts of the outer cage enclose the clot and the elongate inner body in the inverted clot housing configuration.

7. The device of claim 1, wherein the proximal tubular shaft has an outer diameter of less than or equal to 0.021 inches.

8. The device of claim 1, wherein the elongate inner body has an outer diameter of approximately 2.25 mm in the expanded deployed configuration.

9. The device of claim 1, wherein the outer cage has an outer diameter of approximately 5 mm in the inverted clot housing configuration.

* * * * *